(12) United States Patent
Wang et al.

(10) Patent No.: US 7,689,020 B2
(45) Date of Patent: *Mar. 30, 2010

(54) METHOD FOR EXAMINING DEFECT IN PRESTRESSED TENDON AND APPARATUS THEREFOR

(75) Inventors: Chung-Yue Wang, Taipei (TW); Peng-Ching Peng, Jhonghe (TW)

(73) Assignee: National Central University, Taoyuan (TW)

( * ) Notice: Subject to any disclaimer, the term of this patent is extended or adjusted under 35 U.S.C. 154(b) by 832 days.

This patent is subject to a terminal disclaimer.

(21) Appl. No.: 11/583,125

(22) Filed: Oct. 19, 2006

(65) Prior Publication Data

US 2007/0239404 A1    Oct. 11, 2007

(30) Foreign Application Priority Data

Oct. 5, 2006   (TW) .............................. 95137159 A

(51) Int. Cl.
*G06K 9/00* (2006.01)
*G01N 25/72* (2006.01)

(52) U.S. Cl. ........................... 382/128; 382/149; 374/4

(58) Field of Classification Search ................. 382/103, 382/123, 128, 141, 144, 149, 152, 168, 172, 382/181, 184, 189, 199, 203, 219, 132, 254, 382/258, 274, 275, 276, 286–291, 312; 324/642; 378/57, 58; 73/624; 374/4; 392/407
See application file for complete search history.

(56) References Cited

U.S. PATENT DOCUMENTS

| | | | | |
|---|---|---|---|---|
| 5,786,535 A | * | 7/1998 | Takeuchi et al. | 73/624 |
| 5,816,703 A | * | 10/1998 | Yamazaki et al. | 374/4 |
| 6,333,962 B1 | * | 12/2001 | Kitaguchi et al. | 378/57 |
| 6,400,898 B1 | * | 6/2002 | Hawkins et al. | 392/407 |
| 7,075,315 B2 | * | 7/2006 | Tanaka | 324/642 |
| 7,496,172 B2 | * | 2/2009 | Wang et al. | 378/58 |

\* cited by examiner

*Primary Examiner*—Seyed Azarian
(74) *Attorney, Agent, or Firm*—Jackson IPG PLLC

(57) ABSTRACT

A penetrating radiation is used to examine a prestressed tendon in a prestressed concrete. A comparing object is used, whose position and size are known in advance. A magnifying rate of an image size of the comparing object projected on an imaging device is calculated. By using the magnifying rate and by comparing the image sizes of the prestressed tendon and the comparing object projected on the imaging device, the defect size of the prestressed tendon can be figured out.

9 Claims, 2 Drawing Sheets

METHOD FOR EXAMINING DEFECT IN PRESTRESSED TENDON AND APPARATUS THEREFOR

FIELD OF THE INVENTION

Figure 1:
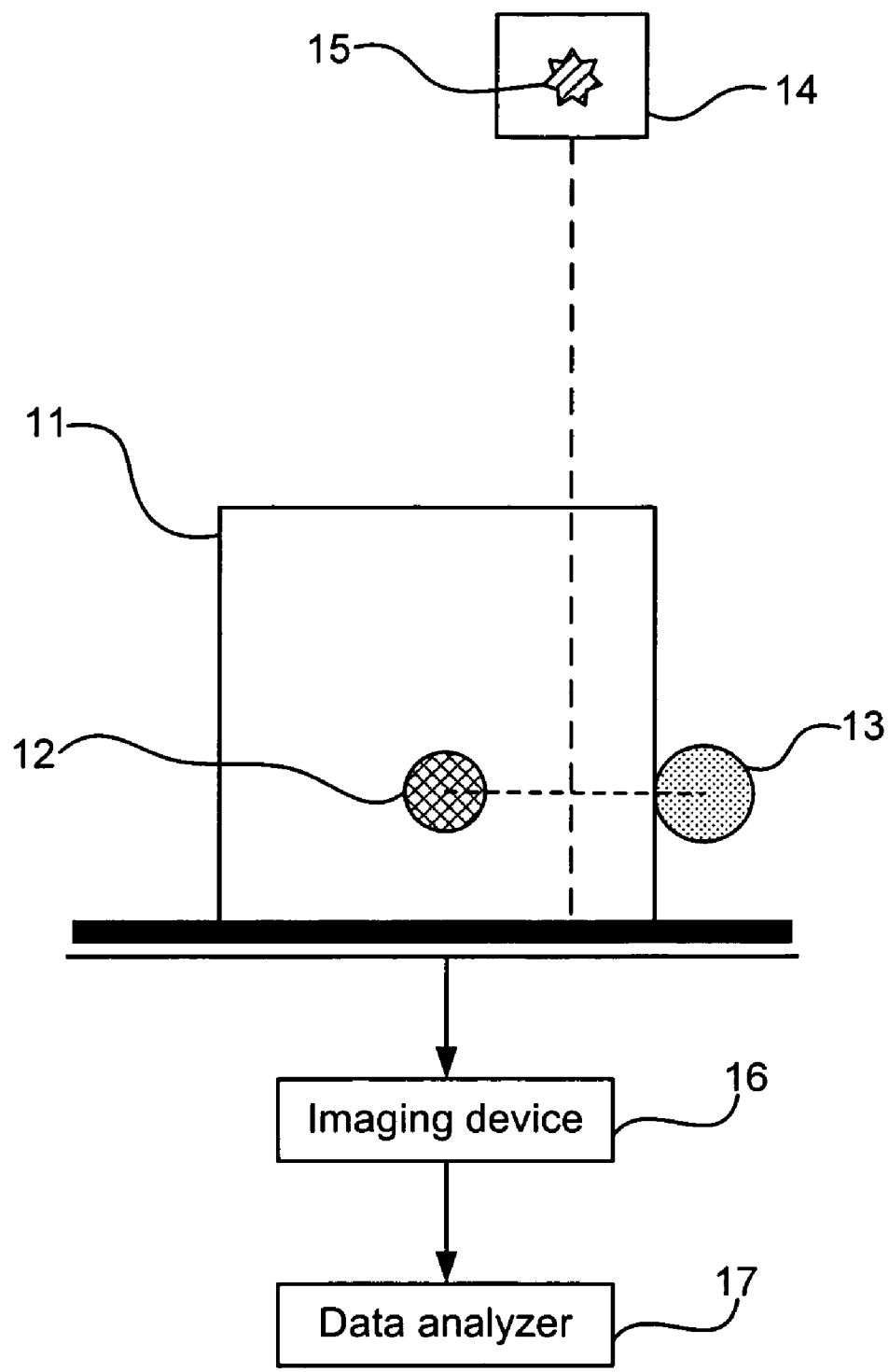

The present invention relates to examining a prestressed tendon; more particularly relates to using a penetrating radiation for examining the prestressed tendon in a prestressed concrete, and using a magnifying rate of image of a comparing object projected on an imaging device for figuring out defect size of the prestressed tendon.

DESCRIPTION OF THE RELATED ARTS

Defect of a prestressed tendon in a prestressed concrete is generally examined by an electromagnetic examination or a potential examination. The above methods all relate to conductivity and potential. But, as chlorine ions grow in the concrete, conductivity grows as well. An interface potential difference happened during a neutralization of the prestressed concrete may be up to 200 milli-volts. Moreover, the concrete is porous where apertures would increase resistance value too. All these situations affect the potential value and the resistance value measured so that fault examination may occur more often. In addition, sleeve covered over the prestressed tendon adds difficulty to the examination. Hence, the prior arts do not fulfill users requests on actual use.

SUMMARY OF THE INVENTION

The main purpose of the present invention is to use a penetrating radiation for examining the prestressed tendon, and use a magnifying rate of an image size of a comparing object for calculating out a defect size of the prestressed tendon.

To achieve the above purpose, the present invention is a method for examining a defect in a prestressed tendon and an apparatus therefor. The method comprises steps of: (a) obtaining a prestressed concrete; (b obtaining a position of a prestressed tendon in the prestressed concrete; (c) locating a spherical comparing object outside of the prestressed concrete to correspond to the prestressed tendon; (d) locating a radiation source outside of the prestressed concrete on a center line between the prestressed tendon and the comparing object for radiating a penetrating radiation; (e) projecting the prestressed tendon and the comparing object on an imaging device with the radiation to measure image sizes of the prestressed tendon and the comparing object; and (f) using the magnifying rate of the image size of the comparing object to calculate defect size of the prestressed tendon.

And, the apparatus for the method comprises a prestressed concrete with a prestressed tendon; a comparing object of a spherical object being located outside of the prestressed concrete and corresponding to the prestressed tendon; a radioactive examining device; a radiation source located in the radioactive examining device on a center line between the prestressed tend on and the comparing object; an imaging device; and a data analyzer, where the radiation source radiates a high-energy ray penetrating through the prestressed tendon to project the prestressed tendon and the comparing object on the imaging device; and the data analyzer analyzes the images to figure out defect size of the prestressed tendon.

Accordingly, a novel method for examining a defect in a prestressed tendon and an apparatus therefor are obtained.

BRIEF DESCRIPTIONS OF THE DRAWINGS

Figure 2:
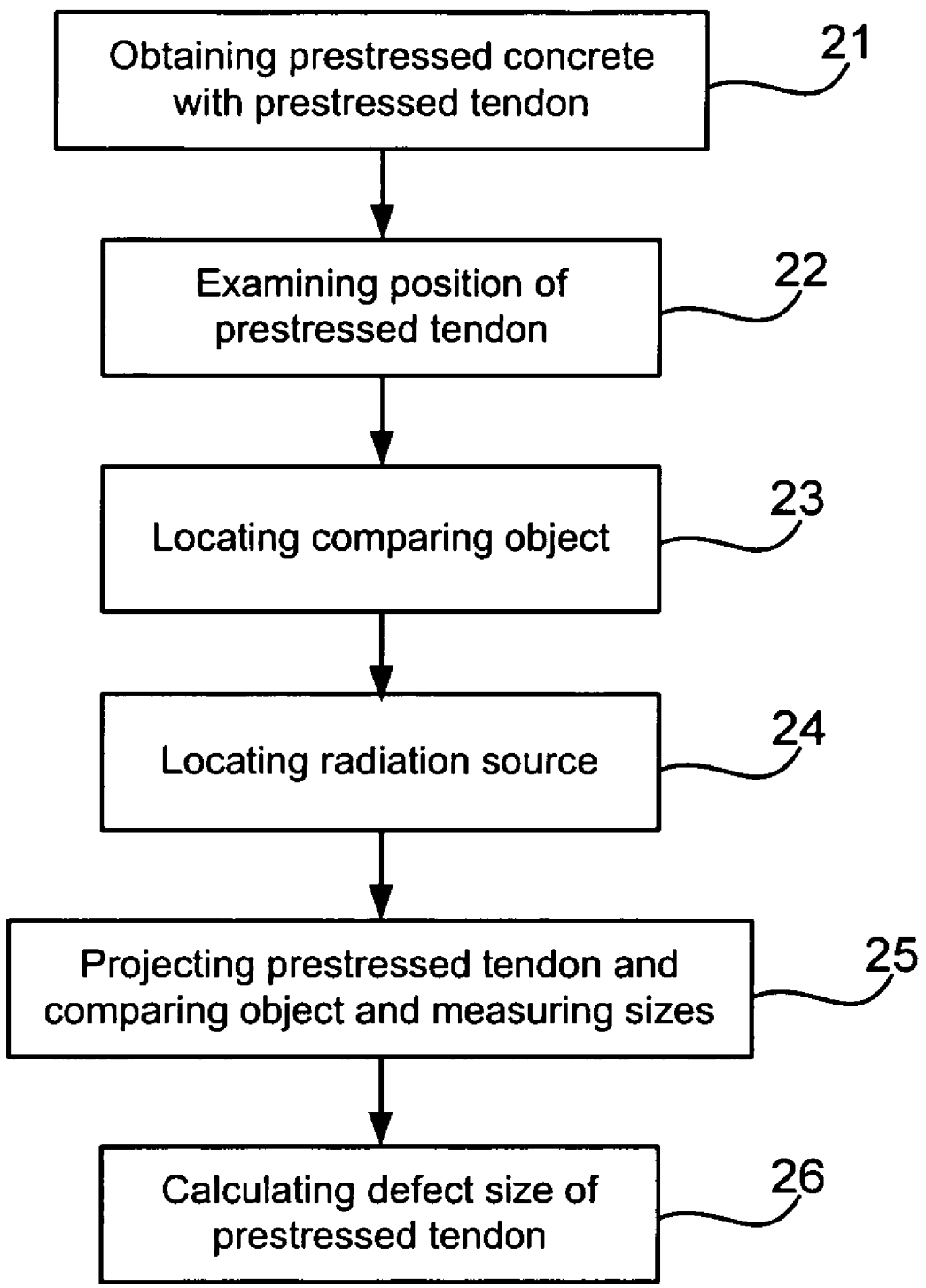

The present invention will be better understood from the following detailed description of the preferred embodiment according to the present invention, taken in conjunction with the accompanying drawings, in which FIG. 1 is the view showing the apparatus of the preferred embodiment according to the present invention; and FIG. 2 is the flow view showing the method of the preferred embodiment.

DESCRIPTION OF THE PREFERRED EMBODIMENT

The following description of the preferred embodiment is provided to understand the features and the structures of the present invention.

Please refer to FIG. 1, which is a view showing an apparatus of a preferred embodiment according to the present invention. As shown in the figure, the present invention is a method for examining a defect in a prestressed tendon and an apparatus therefor. The apparatus comprises a prestressed concrete 11 having a prestressed tendon 12; a spherical comparing object 13 being located outside of the prestressed concrete 11 and corresponding to the prestressed tendon 12; a radioactive examining device 14; a radiation source 15 located in the radio active examining device 14 on a center line between the prestressed tendon 12 and the comparing object 13 to radiate a ray penetrating through the prestressed concrete 11; an imaging device 16; and a data analyzer 17, where the radiation source 15 radiates the ray to project the prestressed tendon 12 and the comparing object 13 on the imaging device 16; and the data analyzer 17 is used to analyze the images projected to figure out defect size of the prestressed tendon. The prestressed tendon 12 can be, for example, a rod or cable or other prestressed support member.

Please refer to FIG. 2, which is a flow view showing a method of the preferred embodiment. As shown in the figure, a method of the preferred embodiment comprises the following steps:

(a) Obtaining prestressed concrete with prestressed tendon 21: A prestressed concrete having a prestressed tendon is obtained.

(b) Examining position of prestressed tendon 22: The position of the prestressed tendon in the prestressed concrete is examined.

(c) Locating comparing object 23: A comparing object is located outside of the prestressed concrete and is a spherical object corresponding to the prestressed tendon.

(d) Locating radiation source 24: A radiation source is located outside of the prestressed concrete on a center line between the prestressed tendon (or inner defect) and the comparing object; the radiation source radiates a penetrating ray of Ir-192, Co-60 or Cs-137;and the radiation intensity of the ray is 75 Ci (Curie).

(e) Projecting prestressed tendon and comparing object for measuring sizes 25: The ray is radiated through the prestressed concrete from the radiation source for projecting the prestressed tendon and the comparing object on the imaging device; and image sizes of the prestressed tendon and the comparing object are measured (f) Calculating defect size of prestressed tendon 26: A magnifying rate of the image size of the comparing object on the imaging device is figured out; and the magnifying rate is used to calculate defect size of the prestressed tendon.

Thus, a novel method for examining a defect in a prestressed tendon and an apparatus therefor are obtained. In the present invention, a characteristic of penetration of a radioactive ray is used for an examination. The radioactive ray has a high energy and an even radiation intensity; the radiation source has a small size no extra energy is required for radiating the ray; and the radiation source can be easily placed at any complex structure. Hence, the radiation source can be located at places for a complete examination; and so the safety of a structure can be evaluated by calculating defect size of the prestressed tendon.

To sum up, the present invention is a method for examining a defect in a prestressed tendon and an apparatus therefor, where a penetrating radiation of low cost and easy operation is used for examination and a magnifying rate of image size of a comparing object projected on an imaging device is used for figuring out defect size of a prestressed tendon.

The preferred embodiment herein disclosed is not intended to unnecessarily limit the scope of the invention. Therefore, simple modifications or variations belonging to the equivalent of the scope of the claims and the instructions disclosed herein for a patent are all with in the scope of the present invention.

What is claimed is:

1. A method for examining a defect in a prestressed tendon, comprising steps of: (a) obtaining a prestressed concrete having a prestressed tendon; (b) obtaining position of said prestressed tendon; (c) locating a comparing object outside of said prestressed concrete; (d) locating a radiation source outside of said prestressed concrete; (e) radiating a ray penetrating through said prestressed concrete to project said prestressed concrete and said comparing object on an imaging device; and (f) obtaining defect size of said prestressed tendon with images obtained after said projecting,
    wherein said radiation source radiates a ray selected from a group consisting of Ir(Iridium)-192, Co(Cobalt)-60 and Cs(Cesium)-137; and wherein said ray has a radiation intensity between 68 Ci(Curie) and 82 Ci.

2. The method according to claim 1, wherein said comparing object is a spherical object.

3. The method according to claim 1, wherein said comparing object is located at a position corresponding to said prestressed tendon.

4. The method according to claim 1 wherein said radiation source is further located on a center line between said prestressed tendon and said comparing object.

5. The method according to claim 1, wherein said method has an apparatus comprising: a prestressed concrete, said prestressed concrete having a prestressed tendon; a comparing object; a radioactive examining device, said radioactive examining device having a radiation source; an imaging device, said imaging device displaying images of said prestressed concrete and said comparing object; and a data analyzer, said data analyzer analyzing and figuring out defect size of said prestressed tendon.

6. The method according to claim 5, wherein said comparing object is a spherical object located at a position corresponding to said prestressed tendon.

7. The method according to claim 5, wherein said radiation source is located outside of said prestressed concrete on a center line between said prestressed tendon and said comparing object.

8. A method for examining a defect in a prestressed tendon, comprising steps of: (a) obtaining a prestressed concrete having a prestressed tendon; (b) obtaining position of said prestressed tendon; (c) locating a comparing object outside of said prestressed concrete; (d) locating a radiation source outside of said prestressed concrete; (e) radiating a ray penetrating through said prestressed concrete to project said prestressed concrete and said comparing object on an imaging device; and (f) obtaining defect size of said prestressed tendon with images obtained after said projecting,
    wherein said method has an apparatus comprising: a prestressed concrete, said prestressed concrete having a prestressed tendon; a comparing object; a radioactive examining device, said radioactive examining device having a radiation source; an imaging device, said imaging device displaying images of said prestressed concrete and said comparing object; and a data analyzer, said data analyzer analyzing and figuring out defect size of said prestressed tendon,
    wherein said comparing object is a spherical object located at a position corresponding to said prestressed tendon.

9. A method for examining a defect in a prestressed tendon, comprising steps of: (a) obtaining a prestressed concrete having a prestressed tendon; (b) obtaining position of said prestressed tendon; (c) locating a comparing object outside of said prestressed concrete; (d) locating a radiation source outside of said prestressed concrete; (e) radiating a ray penetrating through said prestressed concrete to project said prestressed concrete and said comparing object on an imaging device; and (f) obtaining defect size of said prestressed tendon with images obtained after said projecting,
    wherein said method has an apparatus comprising: a prestressed concrete, said prestressed concrete having a prestressed tendon; a comparing object; a radioactive examining device, said radioactive examining device having a radiation source; an imaging device, said imaging device displaying images of said prestressed concrete and said comparing object; and a data analyzer, said data analyzer analyzing and figuring out defect size of said prestressed tendon,
    wherein said radiation source is located outside of said prestressed concrete on a center line between said prestressed tendon and said comparing object.

* * * * *